United States Patent
Verdegan

(10) Patent No.: US 7,788,969 B2
(45) Date of Patent: Sep. 7, 2010

(54) COMBINATION CONTAMINANT SIZE AND NATURE SENSING SYSTEM AND METHOD FOR DIAGNOSING CONTAMINATION ISSUES IN FLUIDS

(75) Inventor: Barry M. Verdegan, Stoughton, WI (US)

(73) Assignee: Cummins Filtration IP, Inc., Minneapolis, MN (US)

(*) Notice: Subject to any disclaimer, the term of this patent is extended or adjusted under 35 U.S.C. 154(b) by 649 days.

(21) Appl. No.: 11/563,792

(22) Filed: Nov. 28, 2006

(65) Prior Publication Data

US 2008/0121026 A1 May 29, 2008

(51) Int. Cl.
*G01N 21/00* (2006.01)
(52) U.S. Cl. .................. 73/61.69; 73/53.01
(58) Field of Classification Search ............. 73/61.69, 73/53.01
See application file for complete search history.

(56) References Cited

U.S. PATENT DOCUMENTS

| | | | |
|---|---|---|---|
| 5,457,526 A | 10/1995 | Kosaka | |
| 5,831,723 A | 11/1998 | Kubota et al. | |
| 5,835,211 A * | 11/1998 | Wells et al. | 356/336 |
| 6,525,325 B1 | 2/2003 | Andrews et al. | |
| 6,794,671 B2 * | 9/2004 | Nicoli et al. | 250/574 |
| 7,127,356 B2 * | 10/2006 | Nicoli et al. | 702/26 |
| 7,496,463 B2 * | 2/2009 | Nicoli et al. | 702/104 |
| 2004/0011975 A1 * | 1/2004 | Nicoli et al. | 250/574 |
| 2004/0109386 A1 * | 6/2004 | Gold et al. | 366/336 |
| 2005/0122522 A1 | 6/2005 | Padmanabhan et al. | |
| 2006/0186899 A1 * | 8/2006 | Gold et al. | 324/665 |
| 2007/0010974 A1 * | 1/2007 | Nicoli et al. | 702/196 |

FOREIGN PATENT DOCUMENTS

| | | |
|---|---|---|
| JP | 8-128944 A | 5/1996 |
| JP | 8-136438 A | 5/1996 |

OTHER PUBLICATIONS

Verdegan et al., "Accurate Methods for Particle Counting.," *Proc. Of the 43rd National conference on Fluid Power*, Chicago, IL, Oct. 11-13, 1988, pp. 299-308.

Verdegan et al., "Advances in Oil Filter Test Methods.", Paper I92-19.1, presented at the International Fluid Power Exposition, Mar. 25, 1992, 12 pages.

Verdegan et al., "Reducing Variability in Particle Count Results for Oil Samples," presented at the International Fluid Power Exposition and Technical Conference, Chicago, IL, Apr. 23-25, 1996, 17 pages.

(Continued)

*Primary Examiner*—Hezron Williams
*Assistant Examiner*—Rodney T Frank
(74) *Attorney, Agent, or Firm*—Hamre, Schumann, Mueller & Larson, P.C.

(57) ABSTRACT

Systems and methods used to monitor a fluid where it is important to know the size, concentration and nature of particulates in the fluid. For example, the systems and method can be used to diagnose contamination issues in fluids such as fuel, lubrication, power transfer, heat exchange or other fluids in fluid systems, for example diesel engines or hydraulic systems, where contaminant particles in the fluids are of concern.

19 Claims, 8 Drawing Sheets

OTHER PUBLICATIONS

Verdegan, "Particle Counting Needs for Oil Applications," NIST Particle Workshop, Gaithersburg, MD, Apr. 25, 2006, 30 pages.

Verdegan, et al., "Using Monodispersed Latex Spheres Dispersed in Nonpolar Liquids to Calibrate Particle Counters," Microcontamimination vol. 8, No. 2, Feb. 1990, pp. 35-39, 64-65.

Verdegan et al., "Recent Developments in Oil Filter Test Methods," Filtration & Separation, Jul./Aug. 1992, pp. 327-331.

Verdegan, "Optical Particle Counter Calibration for Nonpolar Liquid Applications," presented at Filtech 1989, Karlsruhe, West Germany, Sep. 12-14, 1989, 8 pages.

Verdegan et al., "Particle Counting Oil and Water Emulsions," Particulate Science and Technology, vol. 7, 1989, pp. 23-34.

Verdegan et al., "A Systematic Approach for Particle Counting Petroleum Oils," in Liquids and Surface Borne Particle Measurement Handbook, J.Z.Knapp, T. Barber and A. Lieberman 9eds.), Marcel Dekker, Inc., New York, New York (published 1996), pp. 585-635.

International Search Report of PCT/US2007/085614 dated Jun. 16, 2008.

Written Opinion of the International Searching Authority of PCT/US2007/085614 dated Jun. 16, 2008.

* cited by examiner

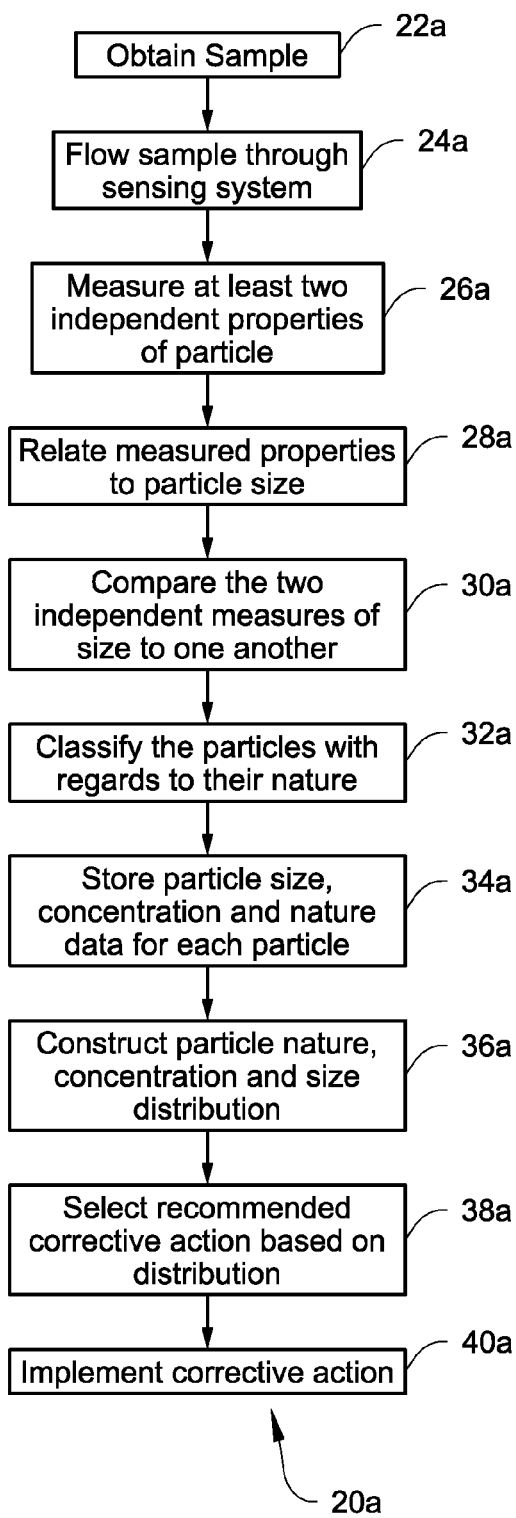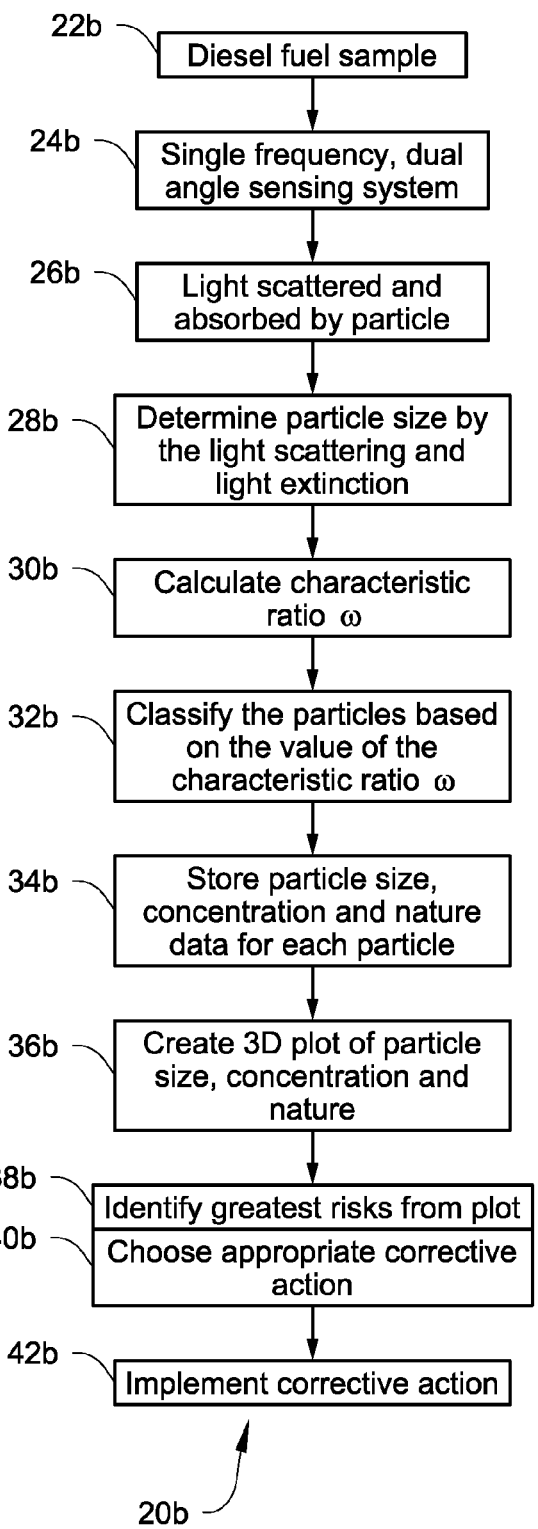

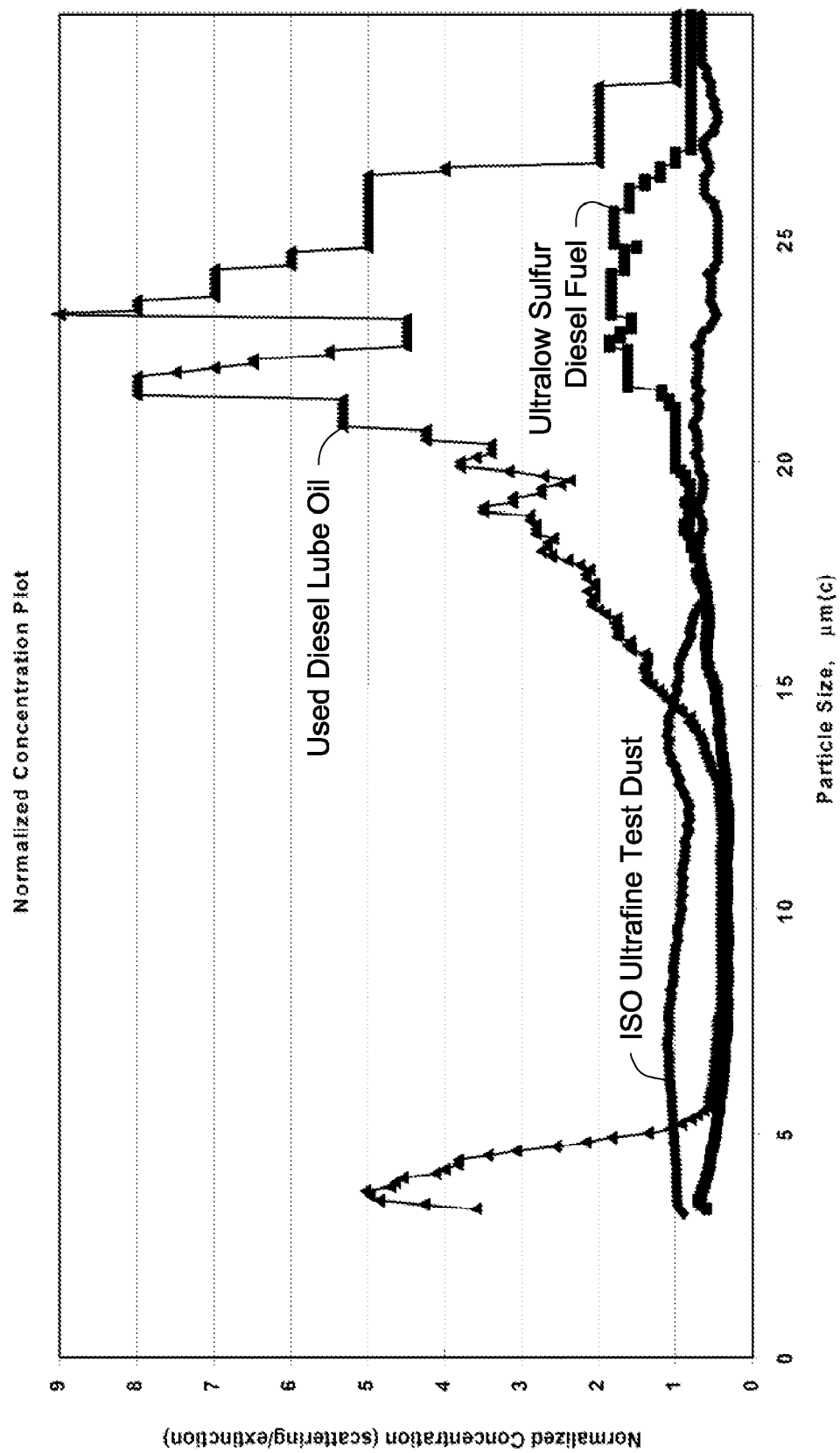

COMBINATION CONTAMINANT SIZE AND NATURE SENSING SYSTEM AND METHOD FOR DIAGNOSING CONTAMINATION ISSUES IN FLUIDS

FIELD

This description relates to the monitoring of fluids where it is important to know the size, concentration and nature of particulates in the fluids. More particularly, this description relates to the diagnoses of contamination issues in a fluid, for example a fluid for fuel, lubrication, power transfer, heat exchange or other fluids in fluid systems where contaminants in the fluids are of concern.

BACKGROUND

In many fluid systems, it is important to know the size, concentration and nature of particulates in the fluid. This is true for both undesirable particles in a fluid (i.e. contaminants) and desired particles in a fluid (i.e. additive particles).

In systems that utilize fluid for fuel, lubrication, transfer of power, and/or heat exchange, it is important that minimum levels of cleanliness with respect to solid and liquid particulates be maintained. Solid and liquid particulates in the fluid can damage system components, shorten life, and reduce performance.

An example of a contamination sensitive system is a high pressure common rail fuel injection system for a diesel engine. A common rail fuel injection system operates at very high pressures with clearances between moving parts approaching 1 µm. Excessive wear of injector components caused by abrasives results in loss of control of fuel injection and increased exhaust emissions. Therefore, fine filters are typically used to protect the fuel injection system. However, these filters are subject to plugging by soft contaminants, such as asphaltenes and biological material. In addition, water droplets can cause corrosion and provide an environment for biological growth to occur. The presence of other particulates in the fuel, such as soot or wear metals, is indicative of other issues. It is clear that there are many possible types of contaminants, and that each type causes different problems and requires a different solution.

In the past, to diagnose and solve a typical contamination-related problem, a significant amount of data in terms of engine history, analysis of failed components, fuel analysis and other data, has been used. However, this data is frequently unavailable or incompletely available, short of significant time and effort on the part of service personnel.

In many cases, the most important data needed to correctly diagnose a contamination problem is the size, concentration and nature of the particulate contamination. For example, with respect to fuel for a diesel engine, it is useful to know whether or not the primary contaminants are harmless air bubbles, corrosive water drops, abrasive silica, or bacteria that plug filters. These different contaminants require different responses. A limitation of conventional diagnostic approaches is that the particulate size, concentration and nature must often be inferred by indirect means. The inference can only be tested by continued use and monitoring of the situation and, may require confirmational testing using non-routine analytical methods. This limits the speed and accuracy of diagnosis, and may result in costly delays in implementing solutions.

A technically possible, albeit impractical alternative diagnostic approach, is a series of specific analyses as soon as a problem is detected, in order to obtain accurate size, concentration and nature data. This is impractical for several reasons. Obtaining all three types of data, even for a single contaminant type, typically requires multiple analyses. For example, to obtain this information with regards to silica would require particle counting (size and concentration data), plus spectrochemical analysis for silicon. When one considers the multitude of contaminant types, it is clear that this is expensive, time-consuming and impractical. Further, there may be more than one contaminant involved, complicating the process of diagnosing and ultimately solving the problem. This is why diagnostic decisions tend to be based on inferences from readily obtainable data, such as engine history, oil analysis, etc. Confirming analyses are only done after there is strong reason to suspect a certain type(s) of contaminant and a more definitive diagnosis is required.

Another issue with conventional approaches is that the particle size and concentration data is divorced from the particle nature data. With the possible exception of laboratory electron microscopic techniques, existing analytical devices provide size and concentration data or nature and concentration data, but do not relate the two. In other words, individual particles are sized and counted, but the supporting chemical analyses tend to be on the bulk or population of particles.

Improved analysis of particles in fluids is needed, including improvements in devices used to analyze the fluids and improvements in the methodology used to analyze data generated by analytical devices.

SUMMARY

This application describes improvements in equipment and methods used to diagnose contamination issues in fluids. The fluids can be fuel, lubrication, power transfer, heat exchange or other fluids in fluid systems, for example diesel engines or hydraulic systems, where contaminant particles in the fluids are of concern. The concepts described herein can be used to monitor any fluid where it is important to know the size, concentration and nature of particulates in the fluid.

Because the shear number of types of contaminant particles in a fluid can be very large, the methodology described herein reduces the data regarding the nature of the particles into a meaningful form from which decisions can be made. To accomplish this, a system that includes the following three features is needed: 1) a sensing system with at least two sensors from which particle size, concentration and nature data can be determined; 2) a methodology of reducing the data into discrete, useful categories upon which to base decisions; and 3) a methodology to relate the categories to appropriate responses for a given situation.

The sensors provide data from which the size, concentration, and nature of contaminant particles in a fluid being sampled can be derived. In one described embodiment, the sensors function together with two light sources that shine collimated light beams through a fluid passage with two sensing volumes containing fluid samples. One of the sensors, each of which can be a photodetector, is associated with each sensing volume for sensing optical properties, for example the amount of light scattered and the amount of light absorbed, of contaminant particles in the fluid samples in the sensing volumes. In another described embodiment, the sensors, which can be photodetectors, function together with a single light source and a single sensing volume in the fluid passage, with the sensors simultaneously detecting optical properties of a contaminant particle in the sensing volume. Although the sensors are said to be photodetectors, one of the sensors could measure and detect, for example, the dielectric constant, electrical conductivity, thermal conductivity, or magnetic properties of particles, and the other sensor could provide particle size data.

The fluid passage can be a channel, tube, orifice, or other flow path oriented normal to the axis of the light beam(s) from the light source(s). The fluid passage needs to confine and direct the fluid, but only needs to be transparent where it encompasses the sensing volume(s) where the light beam(s) enters the fluid (from the side) and leaves the fluid.

The data obtained from the two sensors provides both the size and concentration of the particles, as well as a property of the particles, for example the refractive index. In the described embodiment, the sensors measure the size of particles as defined using a common calibration method. However, because the sensors rely on different operating principles (for example, light extinction and light scattering) or different measurement conditions (for example, different incidence angles, different wavelengths of light, etc.), and have different operational definitions of "size" as a result of their operating principles and/or measurement conditions, they report different sizes depending on the properties of the particle. The comparison of the different operationally defined sizes from the sensors provides previously unknown information about the properties of the particles, which, in turn, tells us about particle nature.

Reducing the data into discrete, useful categories upon which to base decisions can be accomplished by classifying the contaminant particles into general categories, for example based on their material properties, which are useful for solving contamination related problems. The general categories selected will vary depending upon many factors including the type of fluid, the type of fluid system the fluid is used in, the application, and the material property or properties of the fluid and contaminants that are determined from the sensor data. For example, useful categories for fuel filtration (and lubrication, transmission and hydraulic fluid) in a diesel engine include: abrasives, water, biological materials, asphaltenes and organic semi-solids, soot, metals and bubbles. Moreover, for fuel filtration, refractive index is one useful material property that can be used to categorize contaminant particles into these categories. Light absorbance, dielectric constant, and electrical conductivity are other potentially useful material properties.

Once enough individual particles are sized and classified into the categories, the appropriate responses for a given situation can then be determined. For example, in the case of fuel filtration in a diesel engine, excessive abrasives could suggest the need for a filter change or the use of a finer filter; the presence of biological materials could suggest the need for a biocide or supply tank cleaning; and the presence of water could mean that a fuel water separator or that a two-stage coalescer is needed.

BRIEF DESCRIPTION OF THE DRAWINGS

FIGS. 2A and 2B are diagrams of processes of diagnosing contamination issues in a fluid.

FIGS. 7 and 8 are examples of how data from the sensors of the sensing system of FIG. 6 can be presented in graphic form to aid in determining possible contamination.

DETAILED DESCRIPTION

Figure 1:
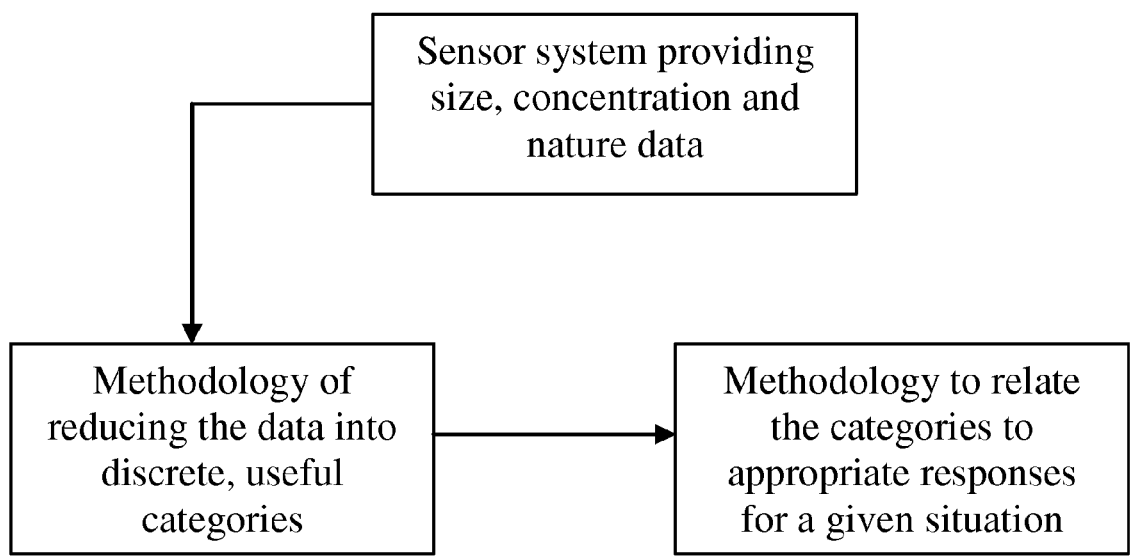
FIG. 1 is a schematic illustration of a system for diagnosing contamination issues in a fluid according to the inventive concepts.

FIG. 1 illustrates a system 10 that can be used to diagnose contamination issues in fluids. The fluids can be fuel, lubrication, power transfer, heat exchange or other fluids in fluid systems, for example diesel engines or hydraulic systems, where contaminant particles in the fluids are of concern. Although the system 10 will be described with respect to the diagnoses of contamination issues, the system 10 can also be used to monitor any fluid where one may consider it important to know the size, concentration and nature of particulates in the fluid, for example process fluids and other fluids for quality control purposes.

The system 10 includes a sensing system 12 that has at least two sensors that generate data on contaminant particles in the fluid from which particle size, concentration and nature data can be determined, a methodology 14 of reducing the data from the sensors into discrete, useful categories upon which to base decisions, and a methodology 16 to relate the categories to appropriate responses for a given situation based on the contaminant particles.

With reference to FIG. 2A, a first embodiment of a process 20a of diagnosing contamination issues in a fluid that is sampled will be described. Initially, a fluid sample is obtained 22a that is then directed 24a through a sensing system 12 of a type later described herein. The sensors of the sensing system 12 measure 26a at least two independent properties of a plurality of individual contamination particles in the fluid sample. Then, in step 28a, the measured properties are related to particle size. In step 30a, the two independent measures of size are compared to one another, and based on the comparison of the independent measures, the particles are classified with regards to their nature in step 32a. The sensors also provide particle concentration data similar to conventional particle counters. The particle size, concentration, and nature data can also be stored 34a, for example in a computer memory. The stored size, concentration and nature data can then be used to, for example, construct 36a a particle size, concentration and nature distribution which can be used to aid in diagnosing the contamination issue. If a contamination problem is found, a suitable corrective action is then selected 38a and implemented 40a to correct the problem.

With reference to FIG. 2B, in the case of a process 20b of diagnosing a contamination issue in, for example, diesel fuel, a sample of diesel fuel is obtained 22b. The fuel sample is then directed through the sensing system 24b having, for example, single frequency, dual angle sensors. Light is directed into the fluid sample in a sensing volume, and the light scattered and absorbed by the particles is measured 26b by the sensors. Particle size is then determined 28b by the light scattering and light extinction. A characteristic ratio ω is then calculated 30b by dividing the size determined by light extinction by the size determined by light scattering. The particles are then classified with regards to their nature 32b based on the value of the characteristic ratio ω. The particle size, concentration, and nature data can also be stored 34b, for example in a computer memory, and the stored data can then be used 36b to create a three dimensional plot of particle size, concentration and nature. The plot can then be used to identify the greatest risks 38b and appropriate action chosen 40b and implemented 42b.

Figure 3:
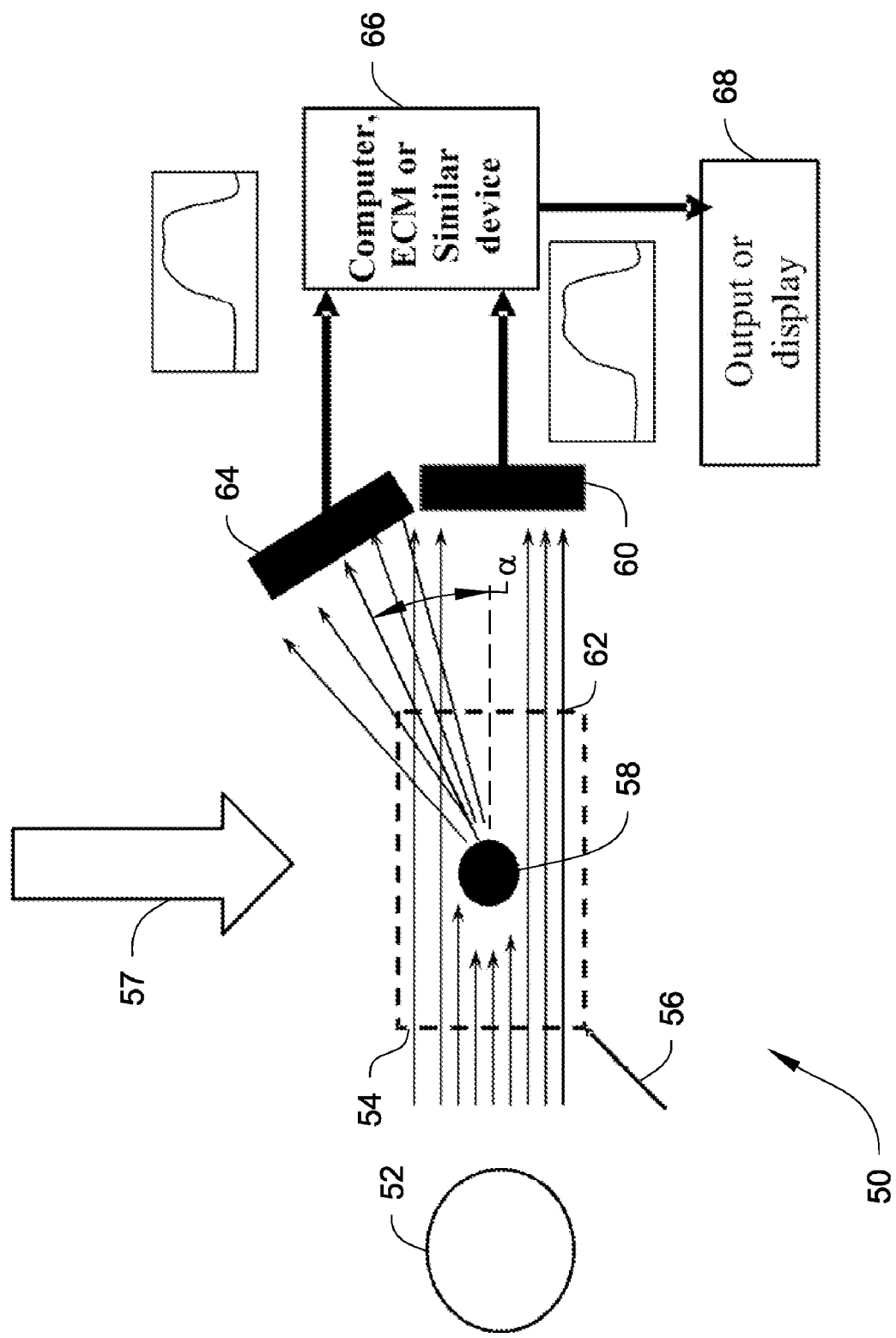
FIG. 3 is a top view of a sensing system that can be used to determine particle size and nature in a fluid being sampled.

FIG. 3 illustrates an example of a suitable sensing system 50 that can be used to implement the processes in FIGS. 2A and 2B. The sensing system 50 includes a light source 52, such as a laser or light emitting diode, which shines a collimated light beam through a transparent window 54 to the fluid within a fluid passage having a sampling volume 56. The fluid sample flows in the direction of the arrow 57 in FIG. 3 in the sampling volume 56, generally normal to the axis of the light beam. Flow through the sensing system 50 could occur due to an associated pump or other means or simply due to a pressure difference across the sensing system 50.

The light beam interacts with a contaminant particle 58 in the sampling volume 56 and is both scattered and absorbed. A sensor 60 in the form of a photodetector located at a first angle $\alpha$ of 0 degrees with respect to the angle of incidence detects the amount of light that passes through another transparent window 62 of the sensing volume. Due to the absorption or the imaginary refractive index by the contaminant particle 58, the amount of light reaching the photodetector 60 is decreased relative to what would be detected in the absence of the particle 58. Further, the reduction is proportional to the cross-sectional area, i.e., the size of the particle 58.

A second sensor 64 in the form of a photodetector is located at a second, different angle $\alpha$ of greater than 0 degrees with respect to the angle of incidence. For example, the photodetector 64 can be located at an angle of between 0 degrees and 180 degrees, preferably at an angle between 10 degrees and 90 degrees. The photodetector 64 detects and measures the amount of light scattered by the particle 58. The amount of light scattered is a function of particle size, real and imaginary refractive index, wavelength of light, and the angle of the photodetector.

With the sensing system 50, each photodetector 60, 64 gives an independent measure of particle size. For each photodetector 60, 64, the precise relationship between particle size and photodetector signal for a specific contaminant is established by means of calibaration according to a suitable calibration standard, for example ISO 11171. Since the angles $\alpha$ of the photodetectors and the wavelength of light are fixed, there are two governing equations. For photodetector 60, the amount of light absorbed is a function of particle size. For photodetector 64, the amount of light scattered is a function of particle size, and the particle's real and imaginary components of its refractive index. In traditional particle counting, it is assumed that the imaginary refractive index of the particles is constant, i.e., the same as that of the particles used to calibrate the instrument. By making that same assumption, that leaves two equations and two unknowns, i.e. the particle size and the real component of its refractive index. This permits the determination of both particle size and real refractive index information for each particle that is detected. To simplify interpretation, it can be assumed that the data from the photodetector 60 is simply a function of particle spherical equivalent cross-sectional area, as is done in ISO 11171. This result can then be used to estimate (the word "estimate" is used since the assumption is made that the imaginary component of refractive index is constant for all particles) the refractive index using data from the photodetector 64. This allows the determination of the particle size as a function of particle nature. By using a third photodetector (not shown) at a third different angle $\alpha$, the information obtained is increased and size, and the real and imaginary components of refractive index can be estimated for a more positive particle identification.

As refractive index is a material property, this information can be used to identify the chemical nature of the particle, in a macro-sense. For example, in the case of diesel fuel, the refractive index can be used to identify the particle as a hard abrasive (e.g., silica), a water droplet, biological material, asphaltene, soot, metal chip, etc. "True" particle size data is obtained from the photodetector 60. Comparison of the results from the two photodetectors 60, 64 gives the nature of the particle. This is turn provides diagnostic information that can be used to troubleshoot or anticipate problems, take corrective action, etc.

Particle size is an inherently useful parameter for solving contamination issues. However, refractive index is only useful if it can be related to the type of contaminant involved. For contamination control, particularly in engine and hydraulic systems, it is not critical that the specific chemical nature of contaminants be known in most cases. Rather, it is generally enough to classify contaminants into categories useful for solving problems. In the case of diesel fuel (and lubrication, transmission and hydraulic fluids), useful classification categories might be as follows: air bubbles, water, biological material, asphaltenes, soot, abrasives, and wear metals.

Figure 4:
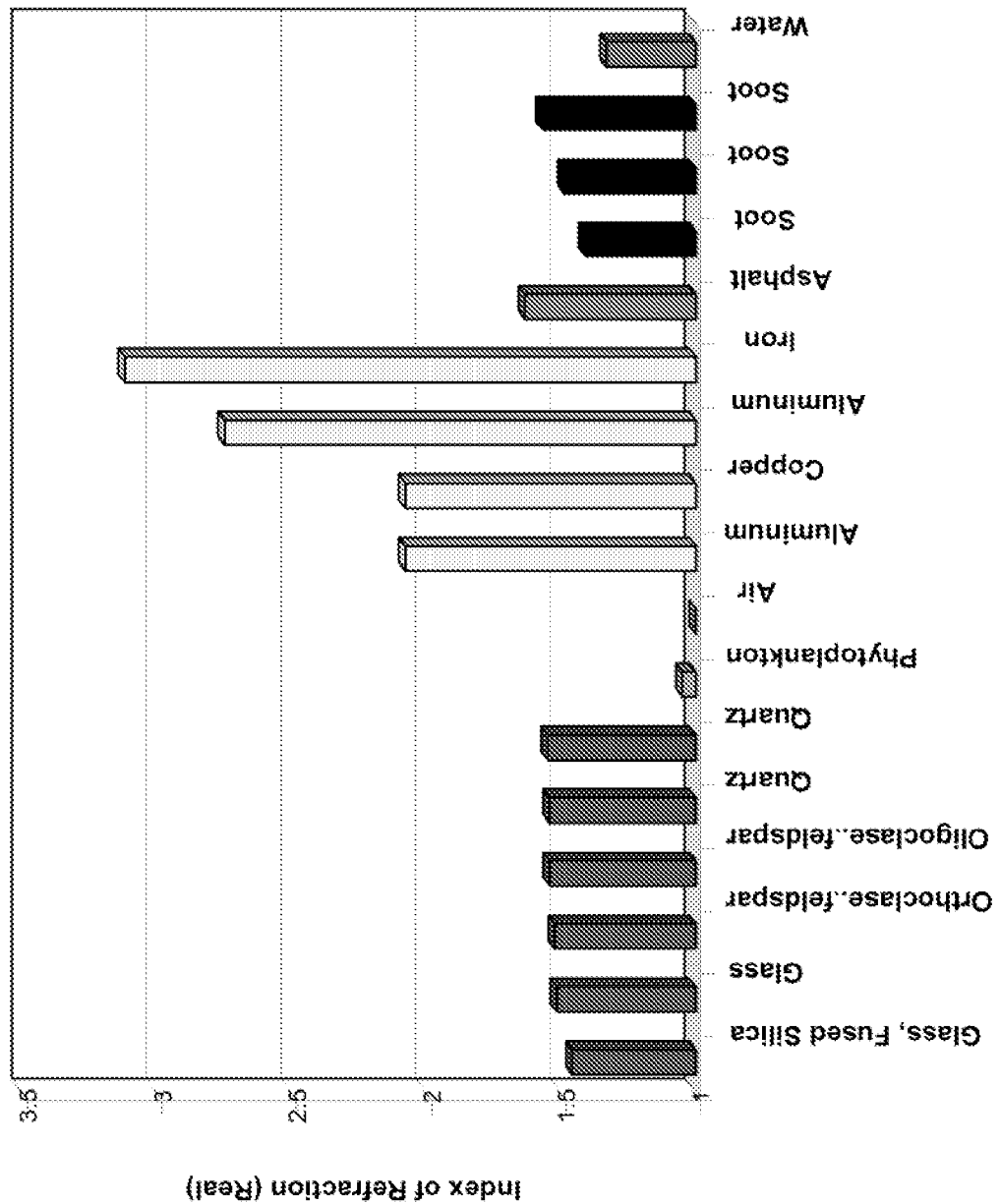
FIG. 4 is an example of a chart illustrating contaminant particles classified into categories based on a material property of the particles.

FIG. 4 shows a histogram of refractive indices of various materials (Y axis) versus their classification. In general, FIG. 4 suggests that, based on refractive index numbers from the literature, that asphalt (a surrogate for asphaltenes), soot, water and biologicals (for example, phytoplankton) can be readily distinguished. It also suggests that, if one limits consideration to metals (for example, aluminum, copper, iron) commonly encountered in engine and hydraulic applications, which typically have refractive indices over 2, this category can also be distinguished. Likewise, with regards to abrasives (for example, fused silica glass, glass, orthoclase or oligoclase feldspar), for engine and hydraulic applications the most interesting abrasives have refractive indices of about 1.5. Thus, the usual materials used in engine and hydraulic applications and the common contaminants can be differentiated by the real refractive index classification scheme shown in FIG. 4. However, other classification schemes, for example those based on light absorptivity, imaginary refractive index, color, dielectric constant, electrical conductivity, and other material properties, could be used.

Alternatively, a third photodetector, which allows determination of the imaginary component of refractive index (or other property of interest), could be used to distinguish classes more accurately. Another possibility is to use size data to facilitate these decisions.

In actual practice, real-world contaminants come in a variety of shapes and tumble (change orientation with respect to the light beam) as they pass through the sampling volume. Hence, the amount of light scattered or absorbed (and the resultant electrical signal from the photodetectors) varies as the particle traverses the sampling volume. Thus, a weighted average of the particle's properties is obtained.

As indicated above, each photodetector 60, 64 should be separately calibrated with respect to size according to ISO 11171 (or with latex or other suitable particle counter calibration technique). The resultant calibration curve gives the relationship between the electrical signal from the photodetector (proportional to the amount of light scattered or absorbed, depending on the angle) for a particular material (silica-based ISO Medium Test Dust, in the case of ISO 11171) and its size. A particle passing though the sampling volume will yield two different apparent particle sizes, size $D_E$ as determined using the photodetector 60, and size $D_S$ as determined using the photodetector 64. When the contaminant particle 58 has optical properties similar to the calibration material, $D_E$ and $D_S$ will be the same as during calibration. When the contaminant particle 58 has optical properties significantly different to the calibration material, $D_E$ and $D_S$ will differ from the values found during calibration.

The ratio of $D_E$ to $D_S$, referred to here as the characteristic ratio, $\omega$, can be used to classify particles according to their nature. The value of the characteristic ratio is primarily a function of the real and imaginary components of refractive index for a particular particle, and to a lesser extent a function of particle size. Thus, the characteristic ratio may be used to characterize particles, instead of using refractive index or other material property. Hard abrasive silicates, such as ISO Medium Test Dust, will have a $\omega$ of approximately 1 (when calibrated according to ISO 11171). Depending on a particle's properties, the ratio may differ.

Figure 5:
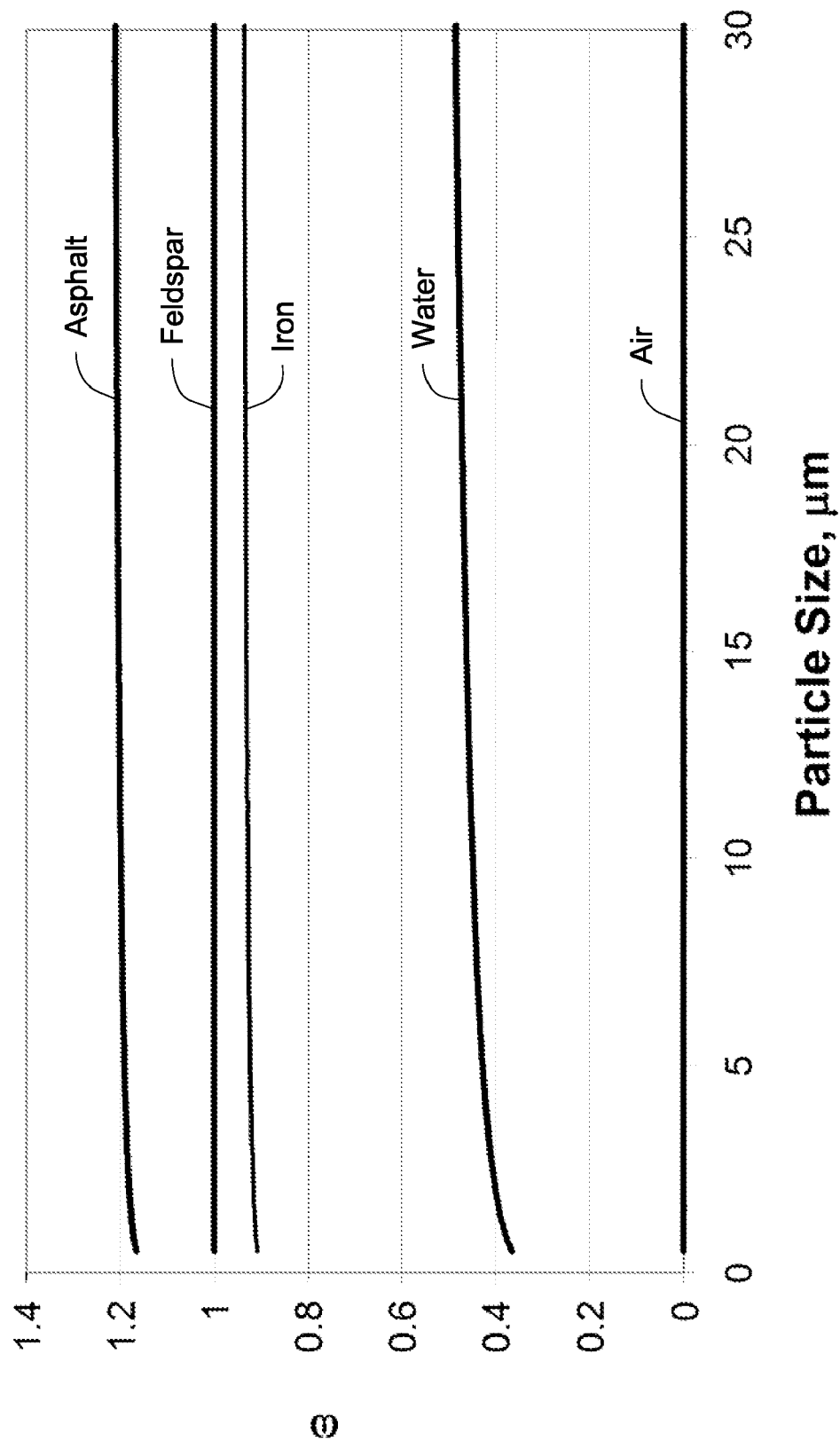
FIG. 5 is plot of characteristic ratio versus particle size for a number of different particles.

FIG. 5 illustrates the results of modeling to demonstrate this approach. In this model, the light source 52 is assumed to be monochromatic, the photodetector 60 is positioned at an angle $\alpha$ of 0 degrees in order to measure the amount of light absorbed, and the photodetector 64 is positioned at an angle $\alpha$ of 90 degrees to measure the amount of light scattered. It is further assumed that the photodetectors 60, 64 are calibrated according to ISO 11171.

Using this model, particles of feldspar (refractive index, $n_D$=1.53), asphalt ($n_D$=1.60), iron (refractive index, $n_D$=1.51), water droplets (refractive index, $n_D$=1.33), and air bubbles (refractive index, $n_D$=1.00) between 1 and 30 µm in size suspended in vegetable oil (refractive index, $n_D$=1.47) are considered. It is assumed that the apparent size determined by the photodetector 60 is independent of the optical properties of the particles, as is commonly assumed in the analysis of oil samples. The amount of light scattered by each type of particle and detected by the photodetector 64 as a function of size was calculated using Mieplot v3418.exe software. From this data, a calibration curve (size as a function of scattering intensity) was constructed by regression of the data to fit a function of the general form:

$$D_S = mI^p$$

where m and p are constants, I is the scattering intensity, and $D_S$ is the particle size. The scattering intensity I is directly related to the photodetector signal. Due to differences in refractive index, each type of particle has a unique calibration curve. Based on these assumptions and models, and using the calibration curves thus obtained, $\omega$ as a function of particle size can be calculated for each type of particle, as shown in FIG. 5.

In actual practice, the calibration curve and resultant $\omega$'s for different types of particles will depend on characteristics of the sensing system, and the properties of the particles and the fluid being analyzed (e.g., oil will yield different $\omega$'s than water).

This modeling demonstrates that:
the sensing system 50 can be used to obtain information concerning the size and type of particles being counted;
that $\omega$ is a property characteristic of the type of particle, but is relatively insensitive to particle size;
the range of differences in $\omega$ suggests that it can be used as a basis for assigning particles to categories useful for contamination control. For example, particles with $\omega \geq 1.1$ have relatively high refractive indices and are probably asphaltenes or soot type particles. Those between about 0.95 and 1.1 tend to be hard, abrasive particles such as silicates. Water is between about 0.3 and 0.5. Air bubbles are less than 0.1.

In addition to the optical features described above, the sensing system 50 preferably allows for fluid flow between the light source and the photodetectors, and the wall of the structure defining the sampling volume 56 is transparent to light and strong enough to withstand the fluid pressure. In addition, the sampling volume 56 needs to be small enough so that only a single particle is detected at a time. The sensing volume is preferably of similar size and flow geometry to that of conventional single particle counters. The sensing volume determines the coincidence error (concentration) limit of the photodetectors. In the past, a guideline has been that the coincidence error limit is:

$$C = (10V)^{-1}$$

$$V = (10C)^{-1}$$

where C is the coincidence error limit of the sensor and V is the sensing volume Thus, the sensing volume typically would be on the order of $10^{-5}$ mL ($10^7$ µm$^3$, or a sensor 100×100×1000 µm in dimension). However, other dimension would work as well.

The sensing system 50 could be used as a laboratory, stand alone device, like conventional particle counters, as a portable device like portable particle counters, or as a sensor mounted and used on-engine or other fluid system or equipment. It could be used to analyze batch samples, such as those collected in a bottle, or for in-line sample analysis.

The sensing system 50 can also include a computer 66 or other data processing device, such as an engine control module (ECM), connected to each photodetector 60, 64 that is suitable to receive signals from the photodetectors, interpret those signals, calculate the particle size and nature data, and store the size and nature data. The data can also be transferred to a suitable output device 68, such as a visual display, to display a two dimensional or three dimensional graph of the particle data.

Once the data is gathered and any graphs, charts or other visual descriptive information prepared showing the size, concentration and classifications of the contaminant particles, the size, concentrations and classifications can be analyzed and decisions made regarding any appropriate corrective actions. For example, a distribution of particle concentration (number or frequency) as a function of particle size and nature can be generated. Visually, this could be represented in tabular form, as a 3D plot, or as 2D slices of the 3D plot. These results could then be used to determine appropriate corrective action. For example, excessive abrasives could suggest the need for a filter change or the use of a finer filter. The presence of biologicals could suggest the need for a biocide or supply tank cleaning. The presence of water could mean the need for a fuel water separator or a two stage coalescer. These suggestions could be in the form of improved filtration, preventative measure, service recommendation, or operation changes.

For some applications, such as on-vehicle sensing systems, it may be unnecessary to display or output the graphs, charts or other output or information descriptive of the contaminant population. Instead, it may be more appropriate to simply display or otherwise output the appropriate state of the fluid or fluid system, corrective actions that should be taken, or even simply to initiate corrective action with or without informing the operator.

The following lists exemplary contaminant particle categories for diesel fuel along with associated responses or preventative measures for each category, and the associated real refractive index for each category.

Functional Categories for Diesel Fuel:
Bubbles—These are typically bubbles of air or fuel vapors formed as a result of cavitation, air leaks or gas entrainment. Depending upon the amount and origin of the bubbles, corrective action may or may not be required.

Biologicals—These are typically the particulate residue from algae, fungi, bacteria, or other living or once living organisms. Corrective action, such as the use of a biocide, extensive tank cleaning, or change in fuel supplier may be needed.

Water—These are typically free or emulsified water droplets. Depending on the location of the sample and conditions of use, the use of a fuel water separator, coalescer or other corrective action may be required.

Asphaltenes and organic semi-solids—These are typically complex, organic semi-solids. These may be the result of a low quality fuel source or generated by overheating in the system. Corrective action may be required to prevent the problem or, if that is not feasible, the use of chemical treatment or a different, more semi-solid tolerant filter to increase service intervals may be in order.

Soot—These are typically carbonaceous byproducts of diesel combustion. This may or may not be due to mixing of lube oil in the fuel or other reasons. Depending on the application, this may or may not be desirable and require corrective action.

Abrasives—These are typically hard minerals, typically oxides normally of natural origin, but could also be oxidation products of metal components from the system. Depending on the size and concentration of these contaminants, a different filtration system, the use of auxiliary filters (e.g. a breather filter), or change in service practices may be required.

Metals—These are typically metal chips and particles resulting from debris left over from the manufacturing process or from wear of the system. A different filtration system, a change in service practices, or investigation of the cause of wear may be necessary.

Operationally Defined (Analytical) Classification* Based on Real Refractive Index:

*numbers are approximate and overlap in some case. The values are based on a representative selection of materials and are not universal. A similar analytical classification based on ω could also be used with somewhat different results.

If n=1.0, then particle is a bubble of air or fuel vapors formed as a result of cavitation, air leaks or gas entrainment.

If $1.0<n<1.3$, then particle is biological in origin, for example the particulate residue from algae, fungi, bacteria, or other living or once living organisms.

If $1.3<n<1.4$, then particle is a water drop, for example a free or emulsified water droplet.

If $1.4<n<1.6$, then particle is an abrasive or soot, for example a hard mineral, typically an oxide normally of natural origin, but also an oxidation product of metal components from the system, or a carbonaceous byproduct of diesel combustion.

If $1.6<n<1.7$ then particle is an asphaltene or organic semi-solid.

If $n>2.0$, then particle is a metal, for example a metal chip or particle resulting from debris left over from the manufacturing process or from wear of the system.

Figure 6:
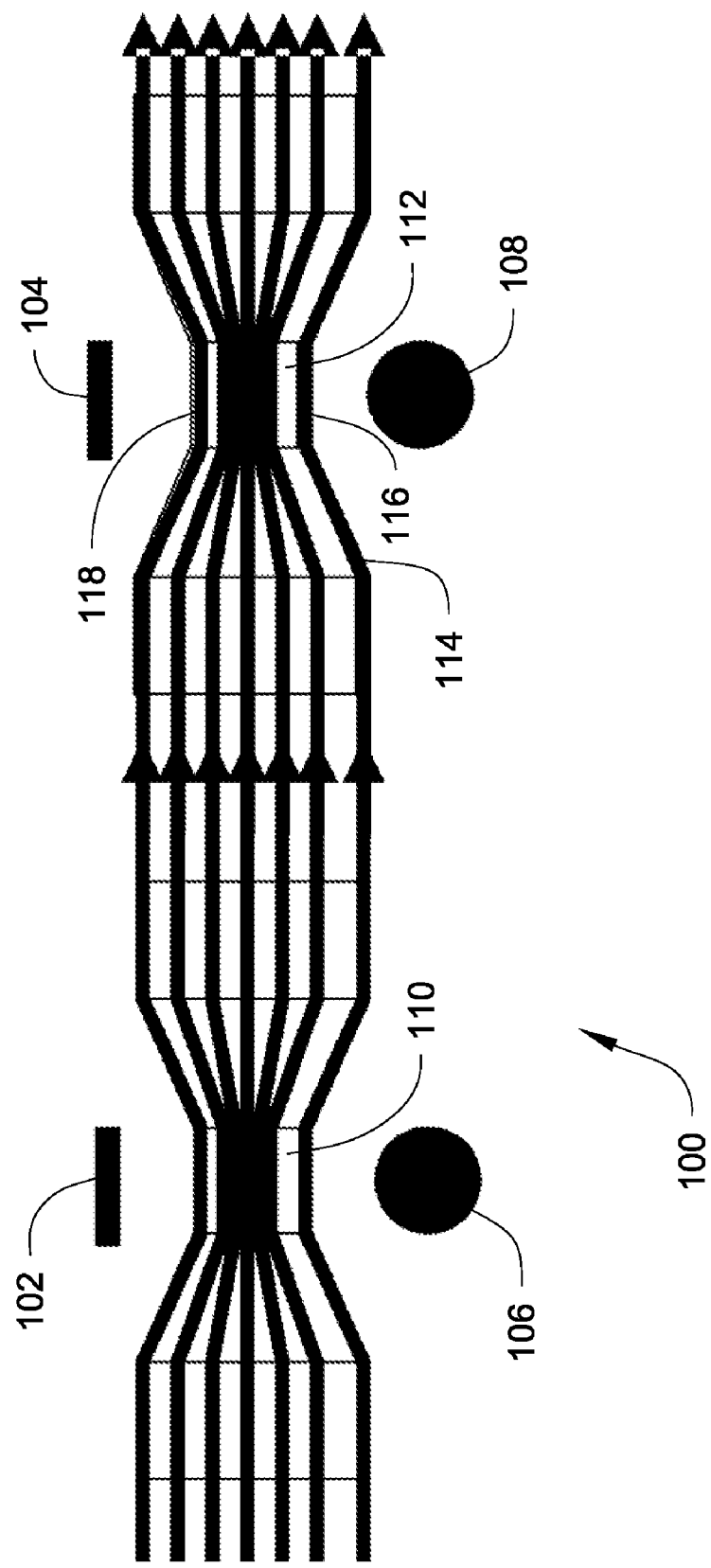
FIG. 6 is a top view of a second embodiment of a sensing system that can be used to determine particle size and nature.

FIG. 6 illustrates another embodiment of a sensing system 100 that can be used to diagnose contamination issues. In the sensing system 50 described above in FIG. 3, two photodetectors are used to simultaneously obtain measurements of two different characteristics of a particle, for example the amount of light absorbed and scattered. The sensing system 50 allows simultaneous determination of the characteristics of a particle, from which its size and nature may be deduced. The information from all of the particles in a sample that flowed through the sensing zone can then be used to obtain descriptive information regarding the entire population of particles in the sample.

The sensing system 100 in FIG. 6 differs in that two (or more) sensors in the form of photodetectors 102, 104 are used in series with each measuring a different characteristic of particles in the fluid. For example, the first photodetector 102 could be a light extinction sensor measuring the amount of light absorbed and the second photodetector 104 could be a light scattering sensor measuring the amount of light scattered. Other arrangements of the two sensors in the sensing system 100 (and the sensing system 50 are possible), for example two scattering sensors could be set at different angles, or two extinction sensors using two different wavelengths of light could be used.

In the sensing system 100, a particle is not simultaneously detected by the two photodetectors 102, 104, hence the size and nature information about a specific individual particle is obtained, but cannot be related to one another. Only information descriptive of the sample population, not of the individual particles making up the population, can be obtained. While less information is obtained than with the sensing system 50, the resultant population information still can provide information concerning the size distribution and nature of the entire population of particles and can be used to diagnose and solve contamination control issues.

The sensing system 100 includes a first light source 106 and a second light source 108, such as lasers or light emitting diodes, which shine collimated light beams into sampling volumes 110, 112 defined by a fluid passage 114. The fluid sample flows in the direction of the arrows in the sampling volumes 110, 112, generally normal to the axis of the light beams from the light sources 106, 108. As with the sensing system 50, flow through the sensing system 100 could occur due to an associated pump or other means or simply due to a pressure difference across the sensing system 100.

The sampling volumes 110, 112 include transparent windows 116, 118 which allow the light beam to enter the sampling volumes, impinge on particles in the fluid within the sampling volumes, and then exit the sampling volumes. The photodetectors 102, 104 are positioned to detect light exiting the sampling volumes. The light beams interact with contaminant particles in the sampling volumes 110, 112 and the light beams are both scattered and absorbed. The photodetector 102 can be positioned, for example being positioned at a first angle α of 0 degrees with respect to the angle of incidence, to detect and measure the amount of light that is absorbed by the particles in sensing volume 110. The photodetector 104 can be positioned, for example being positioned at a second, different angle α of greater than 0 degrees with respect to the angle of incidence, to detect and measure the amount of light scattered by particles in the sensing volume 112. For example, the photodetector 104 can be located at an angle α of between 0 degrees and 180 degrees, preferably at an angle between 10 degrees and 90 degrees.

As with the sensing system 50, each photodetector 102, 104 is independently calibrated, such as according to ISO 11171. Since the same calibration method is used for both photodetectors 102, 104, it is inherently assumed that the particles being analyzed in the unknown sample are similar in terms of their optical characteristics to the calibration material.

A sample is analyzed by flowing the fluid containing particles through the serially arranged sensing volumes 110, 112 of the sensing system 100. As particles pass through the sensing volumes, they are detected by the photodetectors and electrical signals are produced in proportion to some measurable characteristic of the particles, such as the amount of light scattered or absorbed as in the sensing system 50. These signals are processed, sorted and stored to yield a particle size distribution for the sample based on the calibration of the particular photodetector involved. Thus, each photodetector generates its own particle size distribution for the sample. In the case of the sensing system 100 using extinction and scattering photodetectors, it is assumed that the extinction photodetector provides the true particle size distribution, as is normally assumed in particle counting field samples of hydraulic oil. A comparison of the two distributions from the photodetectors provides information concerning the differences in optical properties of the sample particles relative to the calibration material. This allows one to infer not only the contaminant size distribution, but the nature of particles making it up. This information can in turn be used as a basis for making decisions related to optimization of contamination control strategies.

Figure 7:
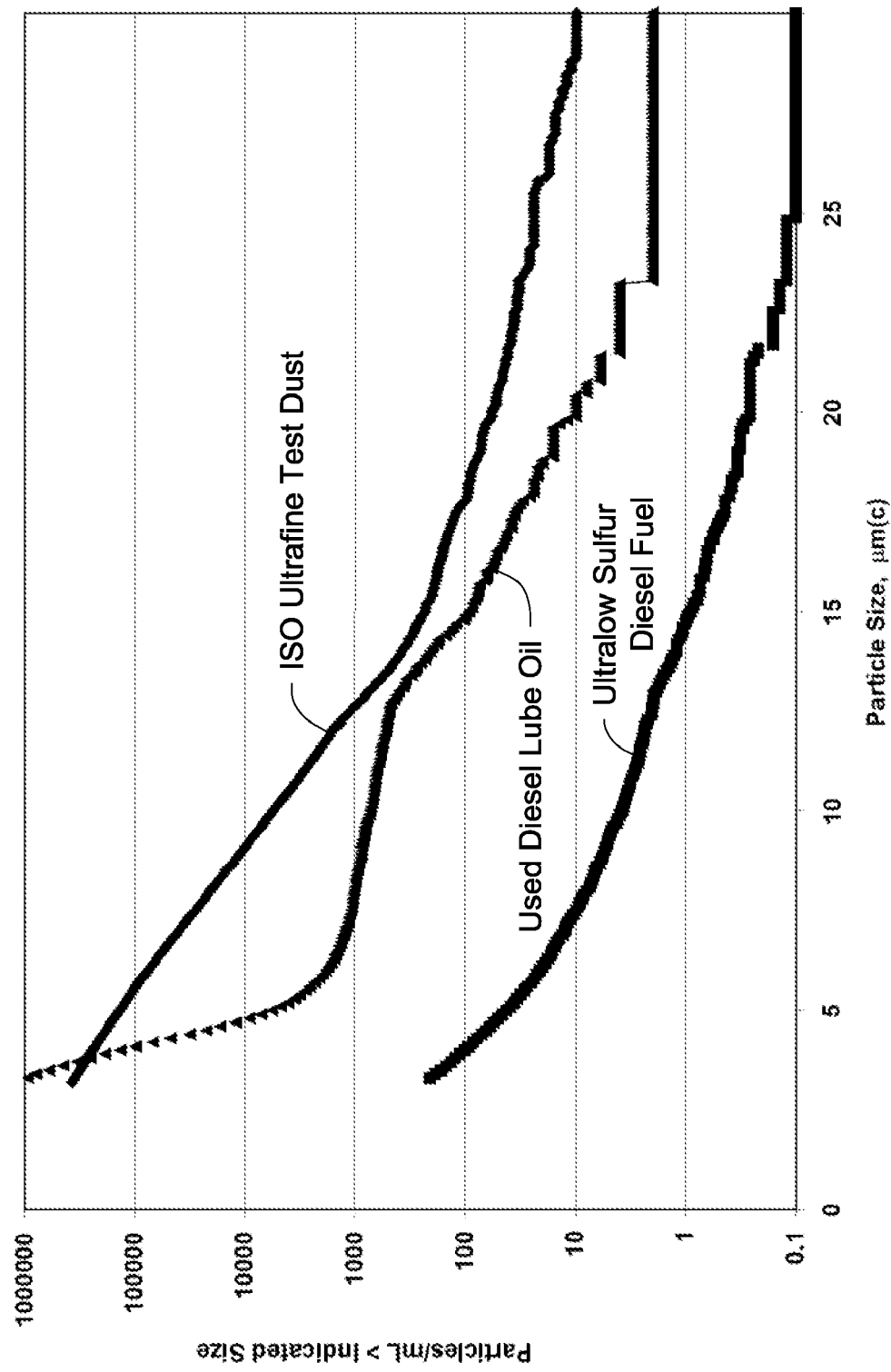

FIGS. 7 and 8 provide an example of the use of the sensing system 100 as part of a contamination control diagnosis. As described, there are two photodetectors 102, 104, a light extinction photodetector and a light scattering photodetector, each of which is calibrated according to ISO 11171. Three samples were analyzed independently with each photodetector in order to generate a light extinction and a light scattering sensor size distribution for each. The data for each sample could be presented in a number of ways, including as a particle size distribution for each photodetector, as particle counts from one photodetector versus particle counts from the other photodetector for the same particle size, as the particle size corresponding to a given number of counts from each photodetector versus one another, as normalized particle concentrations (ratio of concentrations from one photodetector divided by the other) as a function of particle size for one or the other photodetector, or other ways.

FIG. 7 illustrates a plot of the data for the three samples, shown as the particle size distribution as obtained by the light extinction photodetector. From the plot, we can see that ISO Ultrafine (ISO 12103-1, Test dust for filter evaluation—Part 1: Arizona Test Dust) and ultralow sulfur diesel fuel exhibit fairly typical distributions, although the fuel sample is much cleaner, i.e. lower concentrations, than the Ultrafine sample. The lube sample, on the other hand, shows very high concentrations of fine particles as might be expected for such samples with elevated concentrations of soot and fluid recirculating through a lube oil filter.

FIG. 8 illustrates a plot of the normalized concentrations of the samples shown as a function of particle size in order to obtain information concerning the nature of the contaminants. From FIG. 8, it can be concluded that the Ultrafine sample is optically similar to the ISO medium test dust upon which the calibration curve was based. Evidence of this is that the normalized concentrations are approximately 1 for all sizes for which statistically significant numbers of particles were counted, i.e. up to about 15 $\mu$m(c). For the ultralow sulfur diesel fuel sample, the particle concentrations for all but the very smallest size are too low to definitively make such a conclusion. However, indications are that its contaminants, too, are similar to ISO medium test dust. In contrast, for the lube oil, the normalized concentrations are much greater than 1 for sizes smaller than about 5 $\mu$m(c) but lower than 1 for sizes between about 6 and 15 $\mu$m(c). This suggests the presence of at least two types of contaminant that are optically different from ISO medium. One type, primarily present as small particles, scatters light more strongly than the test dust, hence higher counts at the calibrated size than with the extinction sensor. The other type, at sizes from about 6 to 15 $\mu$m(c), that scatters light more weakly than the test dust. At sizes larger than about 15 $\mu$m(c), there are insignificant numbers of counts upon which to base strong conclusions.

From experience, more precise identification of the nature of the two types of particles in the lube oil can be deduced, such as whether they are soot, wear metals, abrasives, or other types of particles, and applied more universally to other types of samples. Thus, the information suggests contamination control strategies to control the fine and mid-range size particles.

In conclusion, whether analysis of the data results from serial sensor measuring particles in the sample population, or from sensor that measure individual particles making up a population, particle size and nature information for the resultant data can be determined and used to diagnose contamination issues and develop contamination control strategies.

The invention may be embodied in other forms without departing from the spirit or novel characteristics thereof. The embodiments disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A method of analyzing particles in a fluid, comprising:
   directing a flow of a fluid to be analyzed into a fluid passage;
   using first and second sensors to obtain data on particles in fluid flowing within the fluid passage, the first and second sensors having been calibrated using the same calibration technique, and the sensors rely on different operating principles or on different measurement conditions; and
   classifying the particles by the nature of the particles based on the obtained data.

2. The method of claim 1, comprising calibrating the sensors using the same size calibration technique.

3. The method of claim 2, wherein the different operating principles comprise light extinction and light scattering, and the different measurement conditions comprise the sensors being disposed at different angles of incidence and/or sensing different wavelengths of light.

4. The method of claim 1, wherein the first and second sensors simultaneously obtain data of a particle in the fluid.

5. The method of claim 1, wherein the sensors are spaced from each other along the fluid passage.

6. The method of claim 1, classifying the particles into particle categories.

7. The method of claim 1, wherein the particles are contaminant particles, the method further comprising
   creating classification categories of contaminant particles commonly found in a fluid that is to be tested for contamination;
   wherein the data obtained using the first and second sensors is data relating to a characteristic of contaminant particles in a fluid sample, and
   wherein classifying by the nature of the particles includes classifying the contaminant particles in the fluid sample into the created classification categories using the obtained characteristic data.

8. The method of claim 7, further comprising
   determining the nature of the particles based on the characteristic data,
   wherein classifying into the created classification categories is based on the nature of particles.

9. The method of claim 7, further comprising one or more of the following based on the classified contaminant particles: generating a visual or audible report, taking corrective action, directly or indirectly informing an operator, suggesting a corrective action to an operator, or interrogating an operator before taking or suggesting a corrective action.

10. The method of claim 1, comprising classifying the particles based on characteristic ratio.

11. A particle size and nature sensing system, comprising:
a fluid passage configured to receive a flow of a fluid to be analyzed;
a first sensor configured to obtain data on particles in fluid flowing within the fluid passage;
a second sensor configured to obtain data on particles in fluid flowing within the fluid passage, and
a processor configured to classify particles in the fluid by the nature of the particles based upon the obtained data on the particles;
wherein the sensors are calibrated using the same calibration technique and the sensors rely on different operating principles or on different measurement conditions.

12. The particle size and nature sensing system of claim 11, further comprising a first light source positioned to direct a light beam into the fluid passage to impinge on particles in fluid flowing within the fluid passage.

13. The particle size and nature sensing system of claim 11, wherein the second sensor is spaced from the first sensor along the fluid passage.

14. The particle size and nature sensing system of claim 11, wherein the first and second sensors comprise photodetectors.

15. A particle size and nature sensing system, comprising:
a fluid passage configured to receive a flow of a fluid to be analyzed;
a first sensor configured to obtain data on particles in fluid flowing within the fluid passage;
a second sensor configured to obtain data on particles in fluid flowing within the fluid passage,
a first light source positioned to direct a light beam into the fluid passage to impinge on particles in fluid flowing within the fluid passage, and
a second light source positioned to direct light into the fluid passage to impinge on particles in fluid flowing within the fluid passage,
wherein the sensors are calibrated using the same calibration technique and the sensors rely on different operating principles or on different measurement conditions.

16. The particle size and nature sensing system of claim 15, wherein the first and second light sources are a laser or light emitting diode.

17. The particle size and nature sensing system of claim 15, wherein the fluid passage includes at least one portion that is transparent to light.

18. The particle size and nature sensing system of claim 15, wherein the second light source is positioned relative to the fluid passage downstream from the first light source.

19. A method of analyzing particles in a fluid, comprising:
directing a flow of a fluid to be analyzed into a fluid passage;
using first and second sensors to obtain data on particles in fluid flowing within the fluid passage, the first and second sensors having been calibrated using the same calibration technique, and the sensors rely on different operating principles or on different measurement conditions;
comparing the data obtained from the first sensor with the data obtained from the second sensor; and
classifying the particles based on the comparison.

* * * * *